United States Patent [19]

Nowak, Jr. et al.

[11] Patent Number: 4,923,695

[45] Date of Patent: May 8, 1990

[54] HYDROCARBON TOLERANT HAIR FIXING COMPOSITIONS

[75] Inventors: Frank A. Nowak, Jr., Somerville; Albert L. Micchelli, Middletown; William M. Rouse, III, Morristown, all of N.J.

[73] Assignee: National Starch and Chemical Corporation, Bridgewater, N.J.

[21] Appl. No.: 292,804

[22] Filed: Mar. 6, 1989

Related U.S. Application Data

[62] Division of Ser. No. 166,332, Mar. 10, 1988, Pat. No. 4,842,852.

[51] Int. Cl.$^5$ ............................................. A61K 7/11
[52] U.S. Cl. ................................... 424/71; 424/78; 424/47; 526/318; 526/319
[58] Field of Search ............................. 526/318, 319; 525/330.3, 329.6; 424/78, 71, 47

[56] References Cited

U.S. PATENT DOCUMENTS

| | | | |
|---|---|---|---|
| 2,996,471 | 8/1961 | Reiter et al. | 424/47 |
| 3,405,084 | 10/1968 | Bohac et al. | 424/47 |
| 3,445,566 | 5/1969 | Skoultchi et al. | 424/47 |
| 3,577,517 | 5/1971 | Kubot et al. | 424/47 |
| 3,723,616 | 3/1973 | Erlemann et al. | 526/518 |
| 3,810,977 | 5/1974 | Levine et al. | 424/47 |
| 3,927,199 | 12/1975 | Micchelli et al. | 424/47 |
| 4,192,861 | 3/1980 | Micchelli et al. | 424/47 |

OTHER PUBLICATIONS

*EPC Application Abstract, Ciba Geigy AG,* Polymer Hair Fixing Formulation–obtd. by reacting acrylic acid, ethylacrylate, and tert.–butyl acrylamide in ethanol (Mar. 23, 1981).
Petter et al., *Kosmetika Aerosole Reichstoff,* Aug. 30, 1987, pp. 427–430.
*Canadian Patent 1,192,135 Ciba Geigy AG,* Hair Setting Preparation (Aug. 20, 1981).

Primary Examiner—Joseph L. Schofer
Assistant Examiner—Jeffrey T. Smith
Attorney, Agent, or Firm—Royal N. Ronning, Jr.; Edwin M. Szala

[57] ABSTRACT

This invention prevents two series of novel hair fixing compositions, the first comprising copolymers of acrylates, N-substituted acrylamides and acrylic acid; and the second comprising copolymers of vinyl acetate or propionate, vinyl esters of α-branched carboxylic acids, and alkyl maleates. Such materials, when neutralized with NaOH, KOH, or mixtures of these bases with certain long chain amines, exhibit an enhanced tolerance of non-halogenated hydrocarbons and are particularly useful.

6 Claims, No Drawings

HYDROCARBON TOLERANT HAIR FIXING COMPOSITIONS

This application is a division of application Ser. No. 166,332, filed Mar. 10, 1988 now U.S. Pat. No. 4,842,852.

1. BACKGROUND OF THE INVENTION

This invention relates to novel hair fixing compositions which exhibit superior hydrocarbon tolerance and are suitable for use in aerosol applications wherein hydrocarbon propellants are used.

In order to be effective in aerosol hair spray formulations, the film forming, polymeric binders utilized therein as well as the films derived therefrom must meet a rigid set of requirements. The binders used in such formulations should be soluble in organic solvents; yet the films cast from such hair spray formulations should, ordinarily, be either water soluble or water dispersible in order to facilitate their easy removal from the user's hair. As is readily visualized, this is an unusual combination of properties which is further complicated by the requirement that the binder used in such formulations be completely compatible with the propellants and solvents ordinarily employed therein. Further, the binders should be stable in the presence of, and unreactive with, the perfumes or other optional ingredients utilized in hair spray formulations.

In addition, the films cast from either aqueous or organic solvent solutions of these binders should be flexible and yet they should have sufficient strength and elasticity; they should adhere well to hair so as to avoid dusting or flaking off when the hair is subjected to varying stresses; they should readily allow the hair to be recombed; they should maintain a nontacky state despite varying environmental conditions; they should be clear, transparent and glossy and should maintain this clarity on aging; they should possess good anti-static properties; and, they should be easily removable by the use of water and/or soap or shampoo.

Many polymeric systems have been utilized in an attempt to meet these stringent requirements. Among these are included; polyvinylpyrrolidone, copolymers of N-vinyl pyrrolidone with vinylacetate, 5-5'-dimethyl hydantoinformaldehyde resins and copolymers of methyl vinyl ethers and maleic acid half esters, etc. Though each of the latter systems has met at least some of the above cited requirements, none has exhibited all of these requirements to an optimum degree.

For example, carboxylated vinyl polymeric hair spray resins, particularly the carboxylated acrylate, and/or acetate based resins, have long been favored for use in aerosol hair spray formulations. Also useful are a class of carboxylated ester polymers comprising an acrylamide, an acidic film forming comonomer, and at least one polymerizable comonomer which are described in U.S. Pat. No. 3,927,199. In order to obtain optimum benefits for the use of such acidic resins, it has been required to neutralize at least a portion, and preferably all, of the available carboxyl functionalities with specific alkaline reagents, e.g. amines and aminohydroxy compounds, as described in, for example, U.S. Pat. Nos. 2,996,471; 3,405,084; 3,577,517; etc. Thus, alkaline reagents which are suggested for such neutralizing include ammonia, lithium hydroxide, potassium hydroxide, sodium hydroxide, mono-, di- or triethanolamine, mono-, di or tripropanolamine, morpholine, amino ethyl ethanol amine, amino methyl propanol, amino methyl propanediol, hydroxy ethyl morpholine, and mixtures thereof. The purpose of this neutralizationn step is both to improve the water solubility or dispersibility of the resin thus permitting easy removal from the hair by merely washing with shampoo and also to affect the degree of flexibility of the resilient film when sprayed on the hair (i.e. to produce a soft film, normal film or a film suitable for "hard to hold" hair). Additionally, U.S. Pat. No. 4,192,861 teaches the use of long chain amines for the neutralization of specific polymers in aerosol hairspray systems.

Recent ecological considerations have resulted in a shift away from the use of certain halogenated propellants and cosolvents and toward the use of hydrocarbons as propellants in aerosol hair spray formulations. In such systems, the binder and any optional ingredients are dissolved in a suitable solvent, such as an alcohol, and the hydrocarbon serves as the propellant. Unfortunately, the use of these propellants produces a number of problems, some of which are due to the decrease in solubility of the binder in the alcohol as the hydrocarbon content is increased to a level acceptable for use as a propellant. Thus, while the carboxylated resins are soluble in the anhydrous alcohol-halocarbon systems of the prior art, and are the commercially preferred resins for their hair holding properties, their reduced solubility in the alcohol-hydrocarbon propellant may render them unacceptable to the industry for use in aerosol systems containing high levels of hydrocarbon propellants.

Thus, there exists a need for hairspray formulations which exhibit desirable hair fixing properties as well as high tolerance of hydrocarbon propellants which are becoming increasingly important in the industry.

2. SUMMARY OF INVENTION

It is an object of this invention to present a series of compositions suitable for use as hair fixing compositions. It is further an object of this invention to present hair fixing compositions which exhibit a high tolerance for hydrocarbon propellants, such that they can be used in aerosol compositions using these propellants.

This invention presents novel hair fixing compositions which comprise a class of copolymers of acrylates, N-substituted acrylamides, and acrylic acid; and a class of copolymers of vinyl acetate or propionate, vinyl esters of α-branched carboxylic acids and alkyl maleates. When neutralized with neutralizing agents containing NaOH, KOH, or mixtures of NaOH and/or KOH with long chain amines such as those described in U.S. Pat. No. 4,192,861, these compositions have been found, quite surprisingly, to exhibit superior tolerance to hydrocarbon propellants used in aerosol hairsprays. This tolerance is especially noticeable at the high levels of neutralization necessary for water removability.

Additionally, the compositions exhibit desirable hair-fixing properties and exhibit a clear, glossy, and durable film when applied to hair.

Since neutralization of the acidic polymers is required for good removability upon shampooing, the copolymers will generally be neutralized prior to incorporation in the hairspray formulation. This neutralization confers a dual benefit on the compositions, increasing not only their shampoo removability but, unexpectedly, their tolerance of high levels of hydrocarbon propellant in the aerosol formulations. This permits a much higher polymer level to be realized in the hairspray formulation and, consequently, a much drier spray. The fact that NaOH and KOH have this effect is surprising in view of the fact that these compounds themselves are not soluble in the non-polar hydrocarbons used as propellants.

3. DETAILED DESCRIPTION OF INVENTION

3.1 POLYMERS USED IN THE HAIRSPRAY FORMULATIONS

3.1.1 ACRYLATE-BASED COPOLYMERS

One class of copolymers especially suited for use in hairspray formulations containing hydrocarbon propellants are copolymers containing 40-60% (by wt.) of a $C_3$–$C_{12}$, preferably $C_3$–$C_8$, alkyl methacrylate, 20-40% (by wt) of a $C_4$–$C_{10}$ N-substituted alkyl acrylamide, and 10-25%, preferably 19-25% (by wt.) acrylic acid or methacrylic acid, wherein the percentages total 100%. More preferably, these copolymers comprise 45-55% isobutylmethacrylate, 25-35% N t-octyl acrylamide, and 19-25% acrylic acid. In a preferred embodiment of this invention, the composition is a copolymer comprising 51% isobutylmethacrylate, 30% N t-octyl acrylamide, and 19% acrylic acid. This polymer is a solid formulation which is soluble in alcohols and other materials which can be used as solvents used in hairspray formulations such as methanol, ethanol, isopropanol, and acetone as well as some other esters and ketones.

These copolymers exhibit superior hair-holding properties and, when applied as an aerosol to the hair, produce a hard, but flexible film which displays excellent subjective properties such as high gloss, good static resistance, and superior adhesion to hair.

These copolymers are insoluble in water, but become soluble when neutralized as described in Section 3.2. This neutralization also confers the distinct benefit of increasing their tolerance to the hydrocarbon propellant, permitting high levels of propellants, often 60-80% or more of the formulation, to be present.

3.1.2 VINYL-BASED COPOLYMERS

In addition to acrylate-based copolymers described above, the class of copolymers of vinyl acetate or vinyl propionate, vinyl esters of $C_5$–$C_{18}$ α-branched carboxylic acids, and monoalkyl maleates exhibit similar properties in terms of hair holding properties and hydrocarbon tolerance. This tolerance is also increased when the copolymer is neutralized.

Typical formulations of these copolymers comprise 20-35% (by wt.) of vinyl acetate or vinyl propionate, 35-50% (by wt.) of a vinyl ester of an α-branched carboxylic acid, and 25-40% (by wt.) of a $C_3$–$C_8$ monoalkyl maleate, wherein the percentages total 100%. More preferably, these copolymers comprise 25-30% of vinyl acetate; 35-40% (by wt), vinyl neodecanoate; and 35-40% (by wt), of a monoisobutyl maleate.

In a preferred embodiment of this invention, the copolymer comprises 25% vinyl acetate, 35% vinyl neodecanoate, and 40% monoisobutyl maleate.

3.1.3 OPTIONAL COMONOMERS

In addition to the copolymers described in 3.1.1 and 3.1.2, the formulations can also contain from 5 to 20% of an optional comonomer. These monomers can be included to tailor and/or enhance certain properties of the copolymer such as hair adherance, hardness, flexibility, antistatic properties and the like. Among these comonomers are acrylic and methacrylic esters of aliphatic alcohols having from 1-12 carbon atoms such as methyl, ethyl, propyl, butyl, octyl and lauryl alcohols; hydroxyalkyl esters of acrylic and methacrylic acids such as hydroxypropyl acrylate and methacrylate, hydroxybutyl acrylate and methacrylate, hydroxystearyl acrylate and methacrylate and hydroxyethyl acrylate and methacrylate; alkyl ($C_1$–$C_4$) and amino alkyl ($C_2$–$C_4$) esters of acrylic and methacrylic acids such as N,N-diethylaminoethyl acrylate, N-t-butylaminopropyl acrylate, N,N-dimethylaminoethyl methacrylate, N-t-butylaminoethyl methacrylate, and the quaternization product of dimethylaminoethyl methacrylate and dimethyl sulfate, diethyl sulfate and the like; diacetone acrylamide; and vinyl esters such as vinyl acetate and vinyl propionate; styrene and alkyl-substituted monomers such as styrene and alpha-methyl styrene; $C_1$–$C_8$ dialkyl maleates; N-vinyl pyrrolidone; and N-substituted alkyl ($C_1$–$C_8$) maleamic acids.

3.2 NEUTRALIZATION

As stated supra, water solubility of acidic polymer compositions used in hairsprays is achieved by neutralization with the appropriate alkaline material, such as NaOH or KOH. An unexpected benefit of neutralization with these materials, however, is that the hydrocarbon tolerance of the copolymers of this invention is greatly increased, permitting high levels of hydrocarbon propellant to be present in the resultant hairspray formulation. Further, since these agents are soluble in alcohol, the polymer compositions can be neutralized directly in the hair spray formulation, eliminating the need for an additional preparation step.

While many alkaline neutralizing agents may be employed to achieve water removability and some degree of hydrocarbon tolerance, maximal hydrocarbon tolerance is achieved by neutralization with NaOH, KOH, and mixtures of NaOH and/or KOH with long chain amines such as those described in U.S. Pat. No. 4,192,861 issued Mar. 11, 1980, to Micchelli et al., and incorporated therein by reference. However, the effect will be observed with any neutralizing agent mixture so long as it contains NaOH and/or KOH as the predominant component.

For the purposes of the invention, the neutralization is preferably as complete as practical. Generally, at least 70%, preferably 80%, and more preferably 90% or more of the carboxyl groups must be neutralized to realize a high degree of hydrocarbon tolerance. While total (100%) neutralization is possible, care must be taken to avoid over-neutralizing the system as the presence of excess neutralizing agents can affect formulation stability.

3.3 HAIRSPRAY FORMULATIONS

In addition to the polymers which are neutralized by the appropriate neutralizing agent as described in Section 3.2, the only other essential ingredients in hairspray formulations are the solvent and the propellant. While in some cases, particularly with chlorofluorocarbons, the propellant can be used as the solvent also, it is anticipated that the materials of this invention will be primarily used with non-halogenated solvents and hydrocarbon propellants (which cannot be used as solvents). In these formulations, the solvents of choice are alcohols, particularly the low boiling, more volatile alcohols.

In general, $C_1$–$C_4$ straight and branched-chain alcohols can be used, with ethanol, propanol, and isopropanol being the preferred solvents. In addition to their excellent solubilizing properties, these solvents are quite volatile (and, thus, evaporate quickly) and are compatable with containers ordinarily used for pressurized aerosols.

While the polymers used in these formulations are compatable with virtually any of the aerosol propellants known to those skilled in the art including halocarbons such as trichlorofluoromethane, it is preferred to use non-halogenated hydrocarbons as the propellants to avoid the release of halocarbons into the atmosphere. Preferred propellants are the lower boiling hydrocarbons, preferably $C_3$–$C_6$ straight and -branched chain hydrocarbons, more preferaby propane, butane, isobutane and mixtures thereof. Other propellants suitable for use in these formulations include ethers such as dimethyl ether.

In general, the method for preparing the hair spray formulations of this invention involves dissolving or diluting the copolymer in the selected solvent(s), adding the neutralizing agent, and subsequently adding any optional compounds whose presence may be desired, and combining the resultant solution with the selected aerosol propellant.

It should be noted that the novel hair spray formulation of this invention will, in all cases, contain at least four essential components. The first and second of these components are the active ingredients which comprise one or more of the above-described copolymers, which serve as the fixative for the formulation, and an appropriate neutralizing agent as described in Section 3.2. The third component comprises one or more solvents which serve as vehicles for the binder. The last component is the propellant which serves to effect the discharge of the aforedescribed fixative and vehicle from the container wherein the formulation is packaged. Water is not ordinarily present, but may be included in some formulations, as may other optional ingredients.

With regard to proportions, the final hair spray formulations typically contain the neutralized polymeric fixative in a concentration ranging from about 0.5 to 12%, by weight; the solvent in a concentration ranging from about 8 to 90%, by weight; and, the propellant concentration ranging from 10 to 85%, by weight, wherein all percentages total 100%. These proportions should, however, be considered as being merely illustrative inasmuch as it may well be desirable to prepare operable formulations having concentrations of components which fall outside the above suggested ranges for particular applications.

As stated supra, optional additives may also be incorporated into the hair fixing formulations of this invention in order to modify certain properties thereof. Among these additives may be included; plasticizers such as glycols, phthalate esters and glycerine; silicones; emollients, lubricants and penetrants such as lanolin compounds, protein hydrolyzates and other protein derivatives, ethylene oxide adducts, and polyoxyethylene cholestrol; U.V. absorbers; dyes and other colorants; and, perfumes. As previously stated, the polymeric binders of this invention show little or no tendency to chemically interact with such additives.

The resulting hair fixing formulations exhibit all of the characteristics required of such a product. Their films are transparent, glossy, flexible and strong. They possess good antistatic properties, adhere well to hair, are easily removed by soapy water or shampoos, allow the hair to be readily recombed, do not yellow on aging, do not become tacky when exposed to high humidities, and have excellent curl retention under high humidity conditions.

4. EXAMPLES

The following examples further illustrate the preferred embodiments of this invention and are not intended to illustrate all embodiments.

4.1 PREPARATION OF COPOLYMERS

In a typical method for the polymerization of acrylate-based copolymers used in the aerosol hair fixing formulations of this invention, a reaction vessel equipped with a condenser and a means for mechanical agitation was charged with 51 parts (by wt.) isobutylmethacrylate, 30 parts (by wt.) N t-octyl acrylamide, 19 parts (by wt.) acrylic acid, 2.0 part (by wt.) benzoyl peroxide, and 100 parts (by wt.) of ethanol. The contents were heated to the reflux temperature of the system and held there for a period of 6 hours whereupon an additional 1.0 part of benzoyl peroxide was added thereto. The system was then held at reflux for an additional 4 hours whereafter the reacton was cooled to 30° C. and the polymer was recovered by standard separation means. This was retained as Sample No. 2.

In a similar preparation, a vinyl-based copolymer was prepared by polymerizing 25 parts (by wt.) vinyl acetate, 35 parts (by wt.) vinyl neo-decanoate, and 40 parts (by wt.) mono-isobutylmaleate as described above. This was retained as Sample 3.

The other polymers evaluated in the subsequent examples were obtained from commercial sources.

4.2 PREPARATION OF AEROSOL FORMULATIONS

In a typical preparation, the hairspray formulations were prepared as follows:

1. The solvent was charged to an agitated mixing vessel at 15°–20° C.;
2. The polymer mixture is then added slowly to assure an even dispersion, and then neutralized to the desired % neutralization by the addition of the neutralizing agent;
3. The mixture is stirred until the neutralized polymer is dissolved and any optional ingredients are then added;
4 The resultant solution is then filtered through a 5–10 micron cartridge filter and subsequently charged, with the appropriate amount of propellant, to an aerosol container on an aerosol charging apparatus.

In this way, a wide variety of aerosol formulations were prepared as set forth in Table I.

TABLE I

Summary of Polymer Systems Used to Prepare Hairspray Formulations

| Monomer | 1[a] | 2[b] | 3[c] | 4 | 5 | 6 | 7 | 8[i] | 9A[f] | 9B[g] | 10[d] | 11[e] | 12[h] | 13 |
|---|---|---|---|---|---|---|---|---|---|---|---|---|---|---|
| vinyl acetate | | | | x | x | x | | | x | x | | | | x |
| crotonic acid | | | | | x | x | | | | | | | | |

TABLE I-continued

Summary of Polymer Systems Used to Prepare Hairspray Formulations

| Monomer | 1[a] | 2[b] | 3[c] | 4 | 5 | 6 | 7 | 8[i] | 9A[f] | 9B[g] | 10[d] | 11[e] | 12[h] | 13 |
|---|---|---|---|---|---|---|---|---|---|---|---|---|---|---|
| vinyl neodecanoate | | | | x | x | x | | | | | | | | |
| t-octylacrylamide | x | x | | | | x | x | | | | | | | x |
| isobutylmethacrylate | | x | | | | | | | | | | | | |
| methyl methacrylate | x | | | | | x | x | | | | | | | |
| hydroxypropyl methacrylate | x | | | | | x | | | | | | | | |
| acrylic acid | x | x | | | | x | x | | | | x | | | |
| t-butylaminoethyl methacrylate | x | | | | | x | | | | | | | | |
| butyl acrylate | | | | | | x | | | | | | | | |
| t-butylacrylamide | | | | | | | | | | | x | | | |
| ethyl acrylate | | | | | | | | | | | x | | | |
| potassium acrylate | | | | | | | | | | | x | | | |
| methyl vinyl ether | | | | | | | | | | | | x | | |
| monobutyl maleate | | | | | | | | | | | | x | | |
| N-vinyl pyrollidone | | | | | | | | x | x | x | | | x | |
| vinyl caprolactam | | | | | | | | | | | | | x | |
| dimethylaminoethyl methacrylate (DMAEMA) | | | | | | | | | | | | | x | |
| monoisobutyl malleate | | | x | | | | | | | | | | | x |

[a] National Starch and Chemical Amphomer ®
[b] an acrylate-based copolymer cf this invention, as prepared in Example 4.1
[c] a vinyl-based copolymer of this invention, as prepared in Example 4.1
[d] BASF "Ultra Hold 8"
[e] GAF Gantrez -ES 425
[f] PVP/VA 70/30 (by weight)
[g] PVP/VA 30/70 (by weight)
[h] GAF Gaffix VC-713
[i] PVP K-30

These polymer samples were used in the subsequent examples using the stated solvent and neutralizing agents, and a hydrocarbon propellant comprising approximately 80% (by wt.) isobutane and 20% (by wt.) propane and designated A-46.

4.3 HYDROCARBON TOLERANCE

To assess the maximum quantity of hydrocarbon which can be tolerated in an aerosol formulation by the neutralized polymer mixtures, the polymer samples were formulated as 2% (by weight) solids using anhydrous ethanol as the solvent and A-46 propellant. The desired degree of neutralization was achieved using the stated neutralizing agent. The propellant was then added to the desired proportion and the formulations, in clear glass tubes, were chilled to $-10°$ C. The maximum amount of propellant tolerated (i.e. that above which phase separation, as evidenced by the onset of turbidity, occurred) at this temperature was observed. The results were as follows:

TABLE II

Results of Hydrocarbon Tolerance Tests

| Polymer Sample No. | % Neutralization | Max. Weight % A-46 Tolerated Neut. Agent | | |
|---|---|---|---|---|
| | | AMP[b] | KOH | KOH/OA[c] (75/25 molar) |
| 1 | 90 | 35-40 | <35 | 30-35 |
| 2 | 90 | 60 | 70 | 80 |
| 3 | 90 | 55 | 70 | 75 |
| 10[a] | 100 | 65 | 65 | 75 |
| 4 | 90 | 25 | — | — |
| 5 | 90 | 30-35 | <30 | 20-25 |
| 6 | 90 | 40-45 | 30-35 | 20-25 |
| 7 | 90 | 30-40 | <10 | 10-25 |
| 11 | 8 | 30-35 | <25 | 55-60 |
| 13 | 90 | <35 | 35 | — |

[a] This sample exhibited a 65-70% tolerance without neutralization
[b] 2-amino-2-methyl-1-propanol
[c] oleyl amine, a long chain amine The above data clearly demonstrate that neutralized acrylate-based (sample 2) and vinyl-based (sample 3) copolymers have exceptionally high tolerances of the hydrocarbon propellant when neutralized by KOH and KOH with a long chain amine. By comparison, similar formulations such as sample 1 and 16 and others did not exhibit this enhanced tolerance when neutralized in the same manner. This is indicative of the superior unexpected behavior of the neutralized copolymers of the instant invention.

By way of comparison, non-ionic (non-carboxylated) polymers exhibit the following tolerances under the same conditions:

TABLE III

Hydrocarbon Tolerances of Non-Ionic Polymer Formulations

| Polymer Sample No. | Max. Weight % A-46 Tolerated |
|---|---|
| 8 | 60-65 |
| 9A | 55 |
| 9B | <50 |
| 12 | 65 |

Thus, it is seen that the hydrocarbon tolerance of neutralized samples 2 and 3 is superior even to that of non-ionic polymers.

4.4 EFFECT OF VARYING SOLVENT

To assess the effect of changing the solvent, a series of experiments identical to those in 4.3 were conducted using isopropanol as the solvent. The results are presented in Table IV.

TABLE IV

Results of Isopropanol Tests

| Polymer Sample No. | % Neutralization | Max. Weight % A-46 Tolerated Neut. Agent | | |
|---|---|---|---|---|
| | | AMP | KOH | KOH/OA (75/25) |

TABLE IV-continued

| 2 | 90 | 60 | 70-75 | 80 |
| 3 | 90 | 55 | 70 | 70 |
| 13 | 90 | <35 | — | — |
| 10 | undet. | | (as received, 70) | |

Once again, samples 2 and 3 exhibited high hydrocarbon tolerances. Sample 10, a commercial hydrocarbon tolerant formulation, exhibited a maximum tolerance of 70. Thus, these formulations of this invention compare favorably with formulation 10 and, in fact, the KOH and KOH/OA neutralized (acrylate-based) formulation (sample 2) is superior to it.

4.5 EFFECT OF VARYING NEUTRALIZING AGENT

To assess the effect of changing the neutralizing agent, a series of experiments were run on Samples 2 and 3, using hydroxides of Group IA elements (alkali metals) in aqueous solution. In each experiment, a formulation containing 2% of neutralized polymer (90% neutralization), 28% anhydrous ethanol, and 70% A-46 propellant was prepared. Neutralization was performed using the indicated base. The mixtures were sealed in glass tubes and gradually chilled until phase separation (as evidenced by the development of turbidity) develops; this temperature is termed the cloud point. The results are presented in Table V.

TABLE V

| Polymer Sample No. | Results of Cloud Point Determinations | | | |
|---|---|---|---|---|
| | Cloud Point (°C.) | | | |
| | LiOH | NaOH | KOH | RbOH |
| 2 | >20° C. | −30 | −32 | >20° C. |
| 3 | >20° C. | −19 | −14 | >20° C. |

The results demonstrate that, even at high hydrocarbon contents, the samples exhibit low, desirable cloud points when KOH and NaOH are used as neutralizing agents; LiOH and RbOH, (which is insoluble in ethanol) do not appear to be good neutralizing agents.

4.6 Effect of Varying Propellants

To assess the effects of varying the propellant used in the formulation, samples 2 and 3, neutralized 90% and KOH, were subjected to the Example 4.3 test to assess the maximum tolerance of dimethyl ether propellant at −10° C. Both samples showed a tolerance in excess of 80%, indicating that they are tolerant of ethers as well as hydrocarbons.

4.7 Subjective Evaluation of Hairspray Formulation

To assess the performance of various formulations samples were prepared and examined for hairspray properties using the following protocol.

1. In a blind study eight clean, dry, 10″ swatches of brown hair are vertically suspended from the bound end.
2. Each front and back is sprayed with the test aerosol for 2 seconds from a distance of 6 inches.
3. A second set of eight swatches is sprayed with the control aerosol in the same manner.
4. Each set is dried 30 minutes at room temperature.
5. The swatches are arranged in pairs consisting of one swatch from each set.
6. Each member of an 8-member panel evaluates the pairs of treated hair swatches is then examined for the following properties:
   (a) Stiffness: Swatches are handled by the panel member and rated in a scale of 1 (soft) to 5 (very stiff).
   (b) Dry Combing: The swatches from the stiffness test are run between the thumb and index finger twice to partially break the "crust". Each swatch is combed gently several times and evaluated as to ease of combout on a scale of 1 to 5. The following rating definitions apply:
   1-no to slight resistance to combing.
   2-moderate resistance.
   3-moderate to severe resistance.
   4-severe resistance to combing; snarling.
   5-complete resistance to combing.
   (c) Adhesion of Hairspray Film to Hair: after the combing test both the hair swatches and the comb are visually inspected for flake accumulation. Swatches are rated on a scale of 1 (no flake appearing) to 5 (severe flake).
   (d) Gloss: Swatches from the flaking (adhesion) test are visually inspected and rated for gloss. A scale of 1 (excellent or high gloss) to 4 (poor) is used.
   (e) Static: Swatches from the gloss test are vigorously combed and rated for the extent of static flyaway generated A scale of 1 (excellent—no static flyaway) to 4 (poor—significant flyaway) is used.

The ratings of the 8 panelists in each determination are averaged and the average is reported. Samples 2, 10, 3 and 4, neutralized to 90% with KOH, were examined in this test series. The results are summarized in Table VI.

TABLE VI

| Polymer Sample No. | Results of Subjective Evaluation Tests | | | | |
|---|---|---|---|---|---|
| | Stiffness | Dry Combing | Adhesion | Gloss | Anti-Static |
| 2 | 2.25 | 2.50 | 1.50 | 1.50 | 2.00 |
| 10 | 2.00 | 1.75 | 1.75 | 1.50 | 2.00 |
| 3 | 2.25 | 2.50 | 1.00 | 1.75 | 1.50 |
| 4 | 2.00 | 1.75 | 2.00 | 1.75 | 1.00 |

It can be seen that the KOH neutralized polymers 2 and 3 not only provide increased hydrocarbon tolerance, but also excellent hair spray formulations which have equivalent or better performance characteristics than conventionally used hair spray polymers.

In is apparent that many modifications and variations of this invention as hereinabove set forth may be made without departing from the spirit and scope thereof. The specific embodiments described are given by way of example only and the invention is limited only by the terms of the appended claims.

What is claimed is:

1. An improved hair fixing composition having increased hydrocarbon tolerance, for use in aerosol formulations, comprising a copolymer of 20–35% (by wt.) of vinyl acetate or vinyl propionate, 35–50% (by wt.) of a vinyl ester of a $C_5$–$C_{18}$ α-branched carboxylic acid, and 25–40% (by wt.) of a $C_3$–$C_8$ monoalkyl maleate, wherein percentages total 100% and all the improvement comprises neutralizing at least 70% of the carboxylic acid functionalities with an alkaline neutralizing agent comprising at least one base selected from the group consisting of NaOH or KOH, such that the tolerance of the copolymer to hydrocarbons is enhanced.

2. The composition of claim 1, wherein at least 90% of the carboxylic acid functionalities are neutralized.

3. The composition of claim 1, wherein the neutralizing agent is NaOH or KOH.

4. The composition of claim 1, wherein the neutralizing agent is a mixture of NaOH or KOH and a long chain amine.

5. The composition of claim 1, wherein the copolymer comprises 25-30% (by wt.) vinyl acetate, 35-40% (by wt.) vinyl neodecanoate, and 35-40% (by wt.) monoisobutyl maleate.

6. The composition of claim 1, wherein the copolymer comprises 25% (by wt.) vinyl acetate, 35% (by wt.) vinyl neodecannoate, and 40% (by wt.) monoisobutyl maleate.

* * * * *